(12) United States Patent
Preiner et al.

(10) Patent No.: US 9,714,901 B2
(45) Date of Patent: *Jul. 25, 2017

(54) MEASUREMENT OF NITRATE-NITROGEN CONCENTRATION IN SOIL BASED ON ABSORPTION SPECTROSCOPY

(71) Applicant: MONSANTO TECHNOLOGY LLC, St. Louis, MO (US)

(72) Inventors: Michael John Preiner, Seattle, WA (US); Nicholas Carleton Koshnick, Palo Alto, CA (US); Justin Stewart White, Palo Alto, CA (US); John Paul Strachan, Millbrae, CA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/009,542

(22) Filed: Jan. 28, 2016

(65) Prior Publication Data

US 2016/0146728 A1 May 26, 2016

Related U.S. Application Data

(63) Continuation of application No. 13/903,841, filed on May 28, 2013, now Pat. No. 9,255,878, which is a
(Continued)

(51) Int. Cl.
*G01N 21/33* (2006.01)
*G01N 21/27* (2006.01)
(Continued)

(52) U.S. Cl.
CPC ............ *G01N 21/33* (2013.01); *G01N 21/00* (2013.01); *G01N 21/276* (2013.01); *G01N 33/24* (2013.01); *G01N 2033/245* (2013.01)

(58) Field of Classification Search
CPC ...... G01N 21/276; G01N 21/00; G01N 33/24; G01N 21/33
(Continued)

(56) References Cited

U.S. PATENT DOCUMENTS 4,389,237 A * 6/1983 Patchett ................. A01N 25/22
504/113
5,117,370 A 5/1992 DeCello et al.
(Continued)

FOREIGN PATENT DOCUMENTS

GB 1202236 A 8/1970
JP 55/035257 3/1980
(Continued)

OTHER PUBLICATIONS

Yamaki, Atsushi, "A Rapid UV Absorption Methods for Determination of Nitrate un Soil Extracts", Japanese Journal of Soil Science and Plant Nutrition, dated Apr. 5, 2003, pp. 195-197.
(Continued)

*Primary Examiner* — Tarifur Chowdhury
*Assistant Examiner* — Isiaka Akanbi
(74) *Attorney, Agent, or Firm* — Hickman Palermo Becker Bingham LLP; Malgorzata A. Kulczycka (57) ABSTRACT

The nitrate-nitrogen concentration in soil is estimated based on the nitrate-nitrogen 200 nm absorption peak. In one embodiment, a device measures the attenuation spectrum of a soil-extractant mixture over a wavelength range that includes wavelengths in the vicinity of the 200 nm absorption peak (the spectral operating range) and then determines the nitrate-nitrogen concentration based on the attenuation spectrum.

22 Claims, 3 Drawing Sheets

Related U.S. Application Data continuation of application No. 12/775,762, filed on May 7, 2010, now Pat. No. 8,472,023.

(60) Provisional application No. 61/215,696, filed on May 7, 2009.

(51) Int. Cl.
  *G01N 33/24* (2006.01)
  *G01N 21/00* (2006.01)

(58) Field of Classification Search
  USPC ............... 356/432, 620, 237.1–237.6; 73/73, 73/54.01, 866; 250/253, 281
  See application file for complete search history.

(56) References Cited

U.S. PATENT DOCUMENTS

| | | |
|---|---|---|
| 2007/0122185 A1 | 5/2007 | Yamazaki et al. |
| 2007/0138401 A1 | 6/2007 | Tokhtuev et al. |
| 2008/0194033 A1* | 8/2008 | Golitz ................... G01N 21/33 436/43 |
| 2008/0291455 A1 | 11/2008 | Holland |
| 2009/0166520 A1 | 7/2009 | Tuli et al. |
| 2010/0283993 A1 | 11/2010 | Preiner et al. |
| 2011/0242530 A1* | 10/2011 | Tuli ................... G01V 9/00 356/300 |

FOREIGN PATENT DOCUMENTS

| | | |
|---|---|---|
| JP | 2002-527740 | 8/2002 |
| JP | 2005-147811 | 6/2005 |
| JP | 2006-145529 | 8/2006 |
| WO | WO0043751 A1 | 7/2000 |

OTHER PUBLICATIONS

Simonsson, Magnus et al., Estimating Nitrate, Dissolved Organic Carbon and DOC Fractions in Forest Floor Leachates Using Ultraviolet Absorbance Spectra and Multivariate Analysis, dated Jan. 2005.
JP 2012-526289.
Japan Patent Office, "Search Report" in application No. 2015-231170, dated Nov. 8, 2016, 4 pages.
Japan Patent Office, "Office Action" in application No. 2015-231171, dated Nov. 8, 2016, 4 pages.
Japan Claims in application No. 2015-231171, dated Nov. 2016, 4 pages.
Japan Claims in application No. 2015-231170, dated Nov. 2016, 6 pages.
Atsushi Yamaki, "A Rapid UV Absorption Method for Determination of Nitrate in Soil Extracts," Japanese Journal of Soil Science and Plant Nutrition, vol. 74, No. 2, pp. 195-197, Apr. 5, 2003.
U.S. Appl. No. 13/903,841, filed May 28, 2013, Office Action, Jun. 6, 2014.
U.S. Appl. No. 13/903,841, filed May 28, 2013, Notice of Allowance, Oct. 1, 2015.
U.S. Appl. No. 13/903,841, filed May 28, 2013, Final Office Action, Nov. 24, 2014.

* cited by examiner

MEASUREMENT OF NITRATE-NITROGEN CONCENTRATION IN SOIL BASED ON ABSORPTION SPECTROSCOPY

CROSS REFERENCE TO RELATED APPLICATIONS

This application claims the benefit as a continuation of application Ser. No. 13/903,841, filed May 28, 2013, which is a continuation of U.S. patent application Ser. No. 12/775,762, filed May 7, 2010, now U.S. Pat. No. 8,472,023, which claims the benefit of U.S. Provisional Application No. 61/215,696, filed May 7, 2009, the entire contents of which are hereby incorporated by reference in their entirety for all purposes as if fully set forth herein.

BACKGROUND

1. Field of Art

The present invention generally relates to measurement of nitrate-nitrogen concentrations in soil.

2. Description of the Related Art

Nutrient levels in soil have significant spatial and temporal variations. Accordingly, there has been significant effort placed into development of local nutrient management schemes, often referred to as "precision agriculture," addressing nutrient level variation. Local nutrient management increases agricultural efficiency while reducing its environmental impact by allowing growers to locally apply nutrients where needed. Increases in nutrient costs and a growing awareness of the environmental consequences of current agriculture practices have made improvements in agricultural efficiency and environmental impact increasingly important.

Nitrate-nitrogen is one of most important nutrients for a variety of crops, but it is particularly mobile in the soil, making it subject to large spatial variations. The conventional approach to nitrate-nitrogen measurement is based on laboratory-based soil measurements. Soil samples are typically mailed to the labs, where the samples are unpacked, sorted, dried, ground, and then measured. This process is fairly expensive and can take up to two weeks before results are available. This can be a significant drawback.

As an example, in-season nitrogen management in corn-growing regions is often difficult because of the slow turn-around time of laboratory-based soil testing. Extending the time when corn growers are able to measure soil nitrogen levels would allow corn growers to test fields before their last application of fertilizer. This would enable corn growers to test fields later in the growing season and implement better nitrogen management practices. Further, allowing growers to promptly retest fields, such as retesting after a rain, would allow growers to adopt more efficient nitrogen management practices. Additionally, laboratory-based soil measurement costs scale directly with the number of samples, making it prohibitively expensive to sample at high grid densities.

As a result, there has been interest in developing faster, simpler and/or less expensive soil measurement techniques to expand the benefits of precision agriculture. Technologies used have ranged from mid-infrared (mid-IR) spectroscopy to ion-selective electrodes. However, each of these methods has suffered from some combination of expense, low accuracy, stringent calibration requirements or difficulty of use.

One approach is based on canopy sensors and satellite imagery that can measure NDVI (normalized difference vegetative index), which is essentially a color measurement that can be used to infer nitrogen needs. These methods are typically fast and operate on a relatively low cost/acre. Unfortunately, there are numerous interferences to NDVI measurements, as many factors can affect crop color, such as water needs and disease. Thus, it appears to suffer from low accuracy. Additionally, this method requires a dense crop canopy to be useful, which puts a tight operational limit on its use. It can only be used fairly late in the season.

There have also been several recent efforts to perform fast "on-the-go" measurements of soil nitrate-nitrogen using ion-selective electrodes. However, the fragility of the ion-selective membrane has caused significant problems with the robustness and reproducibility of soil measurements. Ion-selective systems also require frequent calibration, making them unappealing for routine field use.

Nitrate "strip tests," commonly available from scientific supply stores or from manufacturers, have also been used. However, nitrate strip tests typically suffer from poor accuracy compared to standard laboratory-based tests and require extensive sample preparation, including consumable reagents. For example, the standard preparation time for nitrate strip tests typically approaches 30 minutes, includes numerous preparation steps and requires precise timing of the reaction steps.

In another recent approach, optical absorption has been used for in-situ monitoring of soil nitrate content. However, this approach was based on a filtering method, in which an optical probe was encapsulated inside a porous stainless steel casing. As a result, the method suffered from very slow measurement times (in the tens of hours). In addition, this approach was focused on measuring the nitrate absorption peak at 300 nm. However, the peak at 300 nm has a relatively weak absorption cross section, and so presents difficulties when measuring nitrate concentration values typically found in agricultural soils. For example, experimental results based on the 300 nm peak typically do not demonstrate sensitivity below 100 ppm nitrate-nitrogen concentration, whereas agronomically relevant levels of soil nitrate-nitrogen concentration are in the 0-50 ppm range.

Accordingly, a rapid and economical soil nitrate-nitrogen measurement system could significantly increase the efficiency of agricultural nitrate use.

SUMMARY

The present invention overcomes the limitations of the prior art by estimating the nitrate-nitrogen concentration in soil based on the nitrate-nitrogen 200 nm absorption peak. In one embodiment, a device measures the attenuation spectrum (which could include effects due to scattering in addition to absorption) of a soil-extractant mixture over a wavelength range that includes wavelengths in the vicinity of the 200 nm absorption peak and then determines the nitrate-nitrogen concentration based on the attenuation spectrum. The wavelength range will be referred to as the spectral operating range.

In one implementation, such a device includes a light source, a detector, a sample chamber and a processor. The light source generates light that spans the spectral operating range, including sufficient amounts of light in the vicinity of 200 nm (but not necessarily including 200 nm). The sample chamber holds a soil-extractant mixture (e.g., a water-soil mixture). The light propagates from the light source, through the soil-extractant mixture in the sample chamber, to the detector. Due to the high absorption at 200 nm, the path length through the soil-extractant mixture is short, for example 2 mm or less in many cases. The detector (e.g., a spectrometer) generates a signal that indicates the light received by the detector at different wavelengths across the spectral operating range (the soil spectral signal). The processor uses the soil spectral signal to calculate an attenuation spectrum for the water-soil mixture, and then estimates the nitrate-nitrogen concentration based on the attenuation spectrum. Various approaches are based on analyzing the attenuation spectrum in order to estimate the strength of the nitrate-nitrogen absorption peak at 200 nm.

In one approach, the processor determines the attenuation spectrum based on the soil spectral signal, a reference spectral signal and a dark spectral signal. The reference spectral signal is generated when the sample chamber contains just the extractant without soil, and the dark spectral signal is generated without light from the light source incident on the detector. These three signals can be generated at different times and in different manners. For example, some or all of the signals can be generated at different times using the same equipment. The reference spectral signal and dark spectral signal could be generated as part of a calibration process. A separate reference chamber could be used to generate the reference spectral signal in parallel with the soil spectral signal. Other variations will be apparent.

The spectral operating range is selected to adequately estimate the 200 nm absorption peak, which has a 20 nm full width half max. It usually will also extend into longer wavelengths (e.g., the visible, near IR and/or mid IR) in order to provide enough data to sufficiently account for contributions from other sources (e.g., nitrite-nitrogen, soil scattering, humic acids, organic matter/carbon, inorganic salts, etc.). The light source is selected to provide sufficient power at the wavelengths of interest. The light source preferably has sufficient power at the deep UV range (around 200 nm) relative to the longer wavelengths so that the longer wavelengths do not dominate the detector response.

Once the attenuation spectrum is calculated, the nitrate-nitrogen concentration can be determined using a number of different approaches. The attenuation spectrum around 200 nm includes the nitrate-nitrogen peak but also includes contributions from other sources. These other soil interferences are taken into account when estimating the nitrate-nitrogen concentration. Some approaches are based on physical models of the contributions from different sources. For example, the measured attenuation spectrum can be modeled as the sum of contributions from different sources, where the spectral shape of each contribution is known or modeled. Regression can be used to then determine the relative weights of each contribution, which in turn can be used to estimate the concentration of each source.

In another approach, the contributions from the other soil interferences may be well known or separately determined. These can then be subtracted from the attenuation spectrum, leaving an estimate of the absorption peak at 200 nm. A Gaussian function can be fitted to this residual peak to estimate the nitrate-nitrogen concentration.

Other approaches are more empirical, for example based on training using actual samples with known nitrate-nitrogen concentrations. Partial least squares regression is one possible empirical approach. Partial least squares regression is a multivariate statistical analysis technique that can extract the correlation of the nitrate-nitrogen absorption peak at 200 nm to the nitrate-nitrogen concentration value independent of the background interferences.

In some cases, the processor can also take advantage of time dynamics to estimate concentrations before the soil-extractant mixture actually reaches the steady state concentration. The extraction of soil components has some time constant. It may take some time before the soil-extractant mixture is homogenous with respect to a particular soil component. The concentration can be measured at different times during the extraction process. The data points can then be extrapolated to yield the steady state concentration before the soil-extractant mixture has reached that steady state, thus saving time in the overall process.

The speed with which nitrate is released from soil depends in part on the type of soil and how quickly the soil is broken up. With a more vigorous mechanism for breaking up the soil, nitrate-nitrogen concentration should be estimated in 60 seconds or less, essentially real-time.

The approaches described above can also be combined with other techniques. For example, filtering or centrifuging can be used to process the soil sample. Information obtained from other sources, such as soil type, moisture, conductivity, temperature, ambient humidity and pH, can also be used in the estimate of the nitrate-nitrogen concentration.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF DRAWINGS

The disclosed embodiments have other advantages and features which will be more readily apparent from the following detailed description and the appended claims, when taken in conjunction with the accompanying drawings, in which:

DETAILED DESCRIPTION

The figures and the following description relate to preferred embodiments of the present invention by way of illustration only. It should be noted that from the following discussion, alternative embodiments of the structures and methods disclosed herein will be readily recognized as viable alternatives that may be employed without departing from the principles of the claimed invention.

Figure 1:
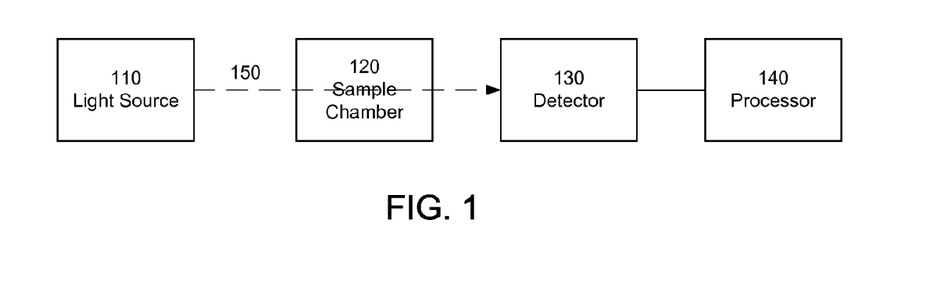
FIG. 1 is a block diagram of a soil analysis device according to the invention.

FIG. 1 is a block diagram of a soil analysis device according to the invention. The device includes a light source 110, a sample chamber 120, a detector 130 and a processor 140. The sample chamber 120 is configured to contain a soil-extractant mixture. It is optically positioned between the light source 110 and detector 130, so that light 150 from source 110 propagates through the soil-extractant mixture and to the detector 130. The processor 140 is coupled to the detector 130.

The device measures the nitrate-nitrogen concentration in soil using the nitrate-nitrogen absorption peak at 200 nm. In this example, the device does this by considering the attenuation spectrum of a soil-extractant mixture across a broad wavelength range (which will be referred to as the spectral operating range) that includes wavelengths in the vicinity of the 200 nm absorption peak.

Figure 2:
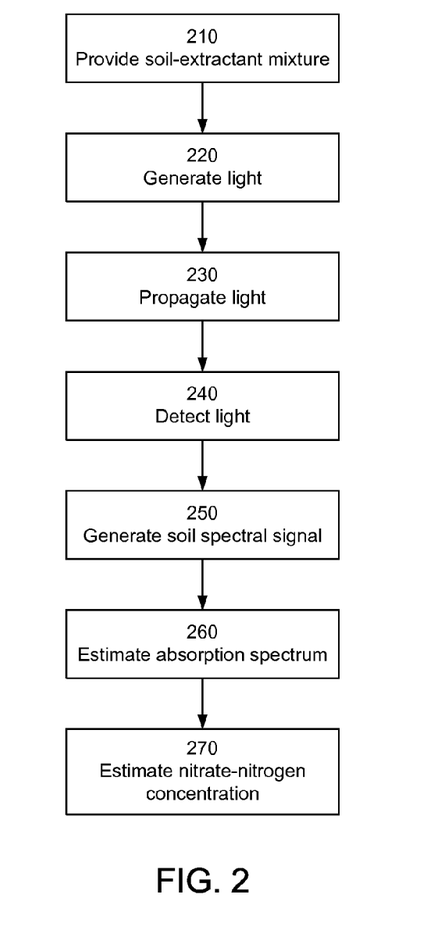
FIG. 2 is a flow diagram illustrating operation of the device in FIG. 1.

FIG. 2 is a flow diagram illustrating the operation of this device. A soil-extractant mixture is provided 210 in the sample chamber 120. The light source 110 generates 220 light that spans the spectral operating range and this light illuminates the sample chamber 120. The light propagates 230 through the soil-extractant mixture and is attenuated by different amounts at different wavelengths. The exiting light is incident on the detector 130 (typically a spectrometer), which detects 240 the amount of light at different wavelengths. The resulting signal generated 250 by the detector 130 will be referred to as the soil spectral signal, to indicate that it is a spectrum across many wavelengths that accounts for attenuation by soil. The detector 130 is sensitive across the spectral operating range. The processor 140 estimates 260 the attenuation spectrum of the soil-extractant mixture based on the soil spectral signal. The attenuation spectrum is calculated over the spectral operating range. The processor 140 then estimates 270 the nitrate-nitrogen concentration based on the attenuation spectrum.

In more detail, the spectral operating range typically includes both the deep UV and the visible. Since this device is based on the absorption peak at 200 nm, the spectral operating range includes wavelengths in the vicinity of this peak in order to estimate the strength of the absorption. For example, the spectral operating range could include (but is not limited to) at least 10 nm to either side of 200 nm (i.e., 190-210 nm or 20 nm full width half max), preferably 20 nm (180-220 nm) or more preferably 30 nm (170-230 nm). The spectral operating range is not required to include 200 nm. The 200 nm absorption peak has a 20 nm width, so wavelengths to either side of the peak can be sufficient to estimate the peak. For example, the spectral operating range may include wavelengths that are only to one side of the peak: 205 nm and longer, 210 nm and longer, or 215 nm and longer. Even ranges as far removed as 230 nm and longer can possibly yield good results depending on the situation. Estimating the 200 nm absorption peak typically determines the lower end of the spectral operating range. More wavelength samples around this peak generally will lead to better results. However, the absorption peak has a 20 nm full width half max, so extending the spectral operating range down to 160-170 nm represents a range of 3-4 widths below the peak.

On the high end, the spectral operating range should be sufficient to account for spectral contributions other than nitrate-nitrogen absorption. Thus, the spectral operating range typically extends into and possibly beyond the visible. Typical spectral operating ranges may extend to somewhere in the 500-1100 nm range on the high end, although wavelengths outside this range are also possible.

Given the low end and high end considerations, typical spectral operating ranges include 150-500 nm, 150-850 nm, 150-1100 nm, 170-1100 nm, 180-1100 nm, 190-500 nm and 190-850 nm. The spectral operating range does not have to be continuous over a wavelength range. For example, if the light source 110 includes multiple devices, the spectral operating range might be 180-220 and 400-800 nm. It might also include discrete sources, sources with tunable emission wavelengths, or narrow wavelength lines.

Figure 3:
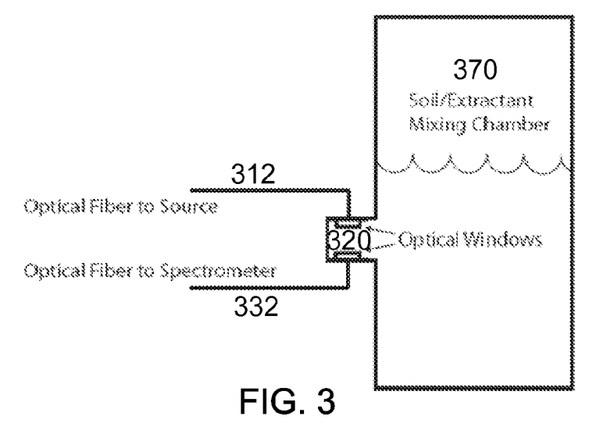
FIG. 3 is a diagram of another soil analysis device according to the invention.

FIG. 3 is a diagram of another soil analysis device according to the invention. In FIG. 3, the light source, detector and processor are not shown. The sample chamber 320 is defined by two quartz optical windows, which transmit well at 200 nm. The incoming light is delivered by fiber 312 and the exiting light is collected by fiber 332. The soil-extractant mixture is created in mixing chamber 370 which is connected to the sample chamber 320.

In one specific design, the light source is a Heraeus UV-Vis FiberLight model DTM 6/50S. This light source has two separately controllable bulbs. One bulb is stronger in the UV compared to the other bulb. Separate controls allows the user or manufacturer to adjust the UV content of the illuminating light relative to the visible content. The optical fibers are standard silica fibers. The detector is a Stellarnet EPP2000C spectrometer, with a wavelength range of 190-850 nm. An alternate detector is the Ocean Optics Maya2000Pro spectrometer, with a wavelength range from 175-1100 nm. The spectrometer wavelength range is narrower than the light source, so the spectrometer determines the spectral operating range which is 190-850 nm or 175-1100 nm in these examples.

The extractant in this example is water. The water-soil mixture is about 1-1.5% soil by weight, for example 5-7.5 g of soil mixed with 460 mL of water. More soil can be used, so long as enough light is transmitted to the detector. For example, higher percentages (5%) of soil can be used with soils that are less optically absorbing. Less soil can also be used, so long as the nitrate-nitrogen signal is sufficiently strong. Other extractants include, but are not limited to, potassium chloride; ammonium fluoride and hydrochloric acid (Bray method); sodium bicarbonate (Olsen method); or ammonium-nitrate, acedic acid, ammonium fluoride, and EDTA (Mehlic method).

The soil is mixed with the water by a motorized stirrer. Other mechanisms such as heating or ultrasound can also be used to increase the speed of extraction of the relevant soil nutrients into the water-soil mixture. Filtering, centrifuging, mechanical separation or other approaches may be used to additionally prepare the mixture. This particular design does not use filtering or centifuging in order to avoid the added complexity and longer processing time.

The water-soil mixture enters the sample chamber 320 and attenuates the light passing through it. Due to the high absorption, the path of the light through the water-soil mixture preferably is short, typically 1 cm or less, generally less than 2 mm.

The spectrometer detects the remaining light after attenuation by the water-soil mixture. This signal is referred to as the soil spectral signal, $I_{soil}$. This spectrometer samples the spectral operating range at 1 nm wavelength increments, or roughly 650 samples over the entire wavelength range. Other wavelength sampling can be used. For example, the sampling may be finer around the 200 nm absorption peak (or any other areas where a narrower spectral feature is expected) and coarser in regions where only broad spectral features are expected. The nitrate absorption peak has a Gaussian width of ~20 nm, which could be reasonably sampled with 5 nm resolution in most cases.

The processor estimates the attenuation spectrum based on the soil spectral signal $I_{soil}$. In this design, it also uses two additional signals: a reference spectral signal $I_{ref}$ and a dark spectral signal $I_{dark}$. The reference spectral signal $I_{ref}$ is the response when the sample chamber is filled with water but no soil. The dark spectral signal $I_{dark}$ is the response when no light is incident on the detector. For example, the light source can be turned off or blocked. The attenuation spectrum is then calculated as $$\alpha(\lambda)=-\log_{10}\{[I_{soil}(\lambda)-I_{dark}(\lambda)]/[I_{ref}(\lambda)-I_{dark}(\lambda)]\} \quad (1)$$

Note that this approach is normalized with respect to spectral variations in source power.

The measurements $I_{soil}$, $I_{ref}$ and $I_{dark}$ can be taken at different times and in different ways with respect to each other. For example, the measurements can be time multiplexed. At one time, the light source is turned off or blocked for $I_{dark}$. At another time, the light source is turned on and the sample chamber filled with water for $I_{ref}$. At a third time, the sample chamber is filled with the water-soil mixture for $I_{soil}$. The different measurements can be made with different frequencies. For example, $I_{ref}$ and $I_{dark}$ do not have to be measured for every sample measurement of $I_{soil}$. In one approach, $I_{ref}$ and $I_{dark}$ are measured periodically (e.g., once per hour, or once per day, or once per some calibration period), or as part of a calibration procedure.

In an alternate approach, the measurements $I_{soil}$, $I_{ref}$ and $I_{dark}$ can be made in parallel using different equipment or multiple optical beam paths. For example, a second chamber can be filled with water. Both the sample chamber and the second chamber (the reference chamber) can be probed at the same time.

Furthermore, not all three measurements $I_{soil}$, $I_{ref}$ and $I_{dark}$ are always required. In some cases, similar or substitute information may be obtained from other sources. For example, if the spectrometer is well characterized and stable, the dark count $I_{dark}$ may be reliably supplied by the manufacturer or determined by some other procedure. As another example, the attenuation spectrum may be estimated based on the intensity of the light before entering the sample chamber and the intensity of the light exiting the sample chamber. Alternately, the reference measurement may be based on a path where the light propagates through air (or through an empty sample chamber) but not water. In some cases, it might be advantageous to have a simultaneous reference measurement of the beam (dual beam system), where the reference beam could pass either through water (without soil) or through just air (no water or soil). Factors such as the absorption of water may be accounted for by models or methods other than direct measurement.

In one approach, the light can take two optical paths, one through the water-soil mixture and another reference optical path not through the water-soil mixture (e.g., through only air without water or soil). The light could be switched between the two paths, or it could be split into two beams, one for each path. The air-only reference measurement $I_{refair}$ is compared to a reference measurement through water no soil $I_{refwater}$. The relationship between the two is assumed to be fairly stable. In the field, the device makes measurements on the water-soil mixture $I_{soil}$ and the air-only reference measurement $I_{refair}$. $I_{refwater}$ can then be determined from Lean based on the previously determined relationship between $I_{refair}$ and $I_{refwater}$.

From the attenuation spectrum $\alpha(\lambda)$, the processor estimates the nitrate-nitrogen concentration. The concentration of nitrate-nitrogen (which has an absorption peak at 200 nm) could be estimated based solely on comparing the attenuation spectrum at 200 nm against standards with known nitrate-nitrogen concentrations. However, the measurement at 200 nm is partly due to nitrate-nitrogen concentration and partly due to other interferences in the water-soil mixture. Thus, the estimate of nitrate-nitrogen concentration can be significantly improved by accounting for these other interferences.

Figure 4A:
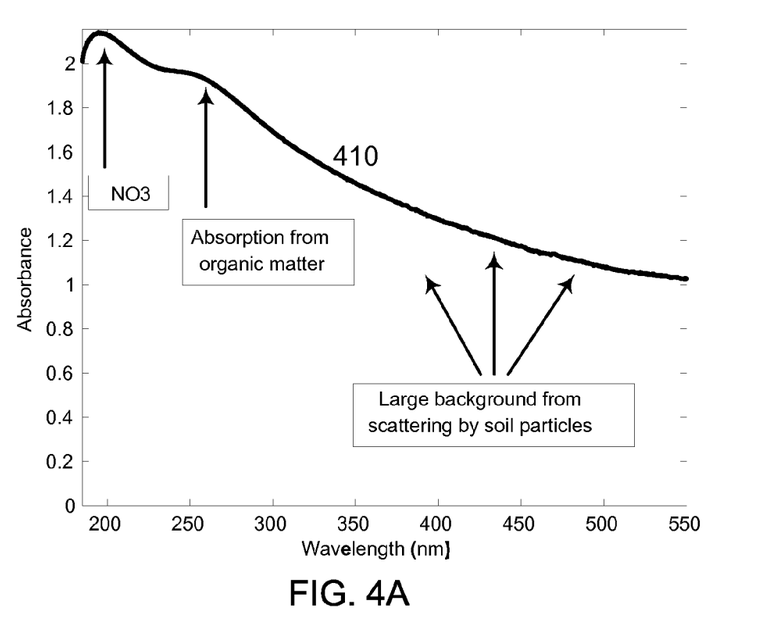
FIGS. 4A and 4B are graphs of an attenuation spectrum, identifying contributions from different sources.

Three common sources of interference to the UV nitrate-nitrogen measurement are scattering from soil particles, humic acids and/or organic matter, and inorganic salts. FIG. 4A is a graph of an attenuation spectrum, identifying contributions from different sources. The curve 410 graphs the attenuation spectrum of an unfiltered, vigorously stirred 50:1 water:soil mixture, taken with a ~1 mm path length cell. The soil has a nitrate concentration (measured via cadmium reduction and a discrete analyzer) of ~8.5 ppm. The spectrum shows a clear nitrate absorption peak near 200 nm, a weaker organic matter absorption peak near 250 nm, and a broad background attenuation (~1 at 500 nm) due to scattering from soil particles.

Figure 4B:
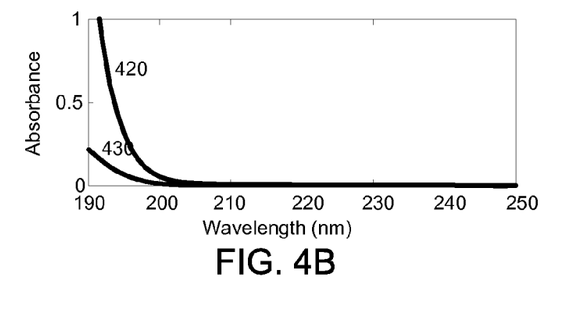

FIG. 4B shows the attenuation spectra of two concentrated solutions of dissolved salts, and illustrates how the spectral shape of the salts is significantly different from that of nitrate-nitrogen. Curve 420 is for 25 mMol KCl, and curve 430 is for 40 mMol $(NH_4)_2SO_4$. As a note, the concentrations used in the graph are much higher than would be found in a typical soil. For example, typical soil levels of 0-1000 ppm K by weight would correspond to 0-20 ppm K in a 50:1 water:soil solution, while the inset shows K levels of ~54,000 ppm by weight in solution. It should also be noted that taking a reference measurement of the water without soil can be used to remove effects of interferences (ions, residual nitrate, etc.) from the water supply, thus eliminating the need for distilled or purified water.

Different approaches can be used to account for these interferences. Some are based on physical models of the contributions from different sources. Others are more empirical, for example training based on actual samples with known nitrate-nitrogen concentrations.

At the preferred water:soil ratios of 20:1 or less, the scattering from soil particles is expected to present the largest background signal. However, the spectral shape of this background (which shows up as a broad absorption/extinction that steadily increases at shorter wavelengths) is different from the absorption of nitrate, which has a well-defined, Gaussian shape with a peak at 200 nm and a Gaussian width of 20 nm. As a result of this spectral shape, spectral deconvolution and curve-fitting techniques may be used to effectively remove this interference. Additionally, if needed, flocculents or salts could be added to decrease the turbidity of the water soil mixtures, although these materials should be chosen so as not to absorb in the UV region of interest.

Organic matter and humic acids are additional potential sources of interference due to their absorption in the UV. This is primarily due to conjugated carbon-carbon bonds which typically absorb around 254 nm, although this can vary depending on the particular molecular species present. Appropriate curve-fitting algorithms may be used to remove the effect of these spectrally distinct interferences. Additionally, soil organic matter in agricultural soils is typically 1-10% as measured with the loss-on-ignition technique, and only a small fraction of this is reactive (conjugated) carbon, so the magnitude of these interferences is expected to be relatively small.

Some inorganic salts (such as KCl, NaCl, etc) can also absorb in the deep UV when dissolved in solution. However, as with organic matter, the spectral shape of this absorption is typically quite different from the absorption spectrum of nitrate-nitrogen, typically consisting of a relatively sharp increase in absorption with decreasing wavelength that extends to below 190 nm. See the inset of FIG. 4, for example. This distinct shape allows removal of this interference with appropriate curve-fitting algorithms.

In one approach, the attenuation spectrum is modeled as consisting of the two nitrate-nitrogen absorption peaks (modeled as Gaussian curves at 201 nm and 302 nm), and one or more Gaussian curves to account for nitrite, organic/humic matter absorption, and Rayleigh background attenuation. By performing this type of analysis on a representative set of soils, the optimal fitting parameters to remove background interferences can be determined. An example of a possible fitting algorithm is shown below $$\text{Abs} \propto C_{Nitrate} e^{-\left(\frac{\lambda - \lambda_{Nitrate}}{w_{Nitrate}}\right)^2} + \sum C_j e^{-\left(\frac{\lambda - \lambda_j}{w_j}\right)^2} + (B_R - A_R \log \lambda) \qquad (2)$$

where $\lambda$ is the wavelength, $w_j$ is the width of the absorption peak for the species of interest, $\lambda_j$ is the center of the absorption peak, the sum over the $C_j$ terms are for potential absorption interferences (such as nitrite, organic matter, etc.), and the $A_R$ and $B_R$ account for Rayleigh scattering.

Figure 5:
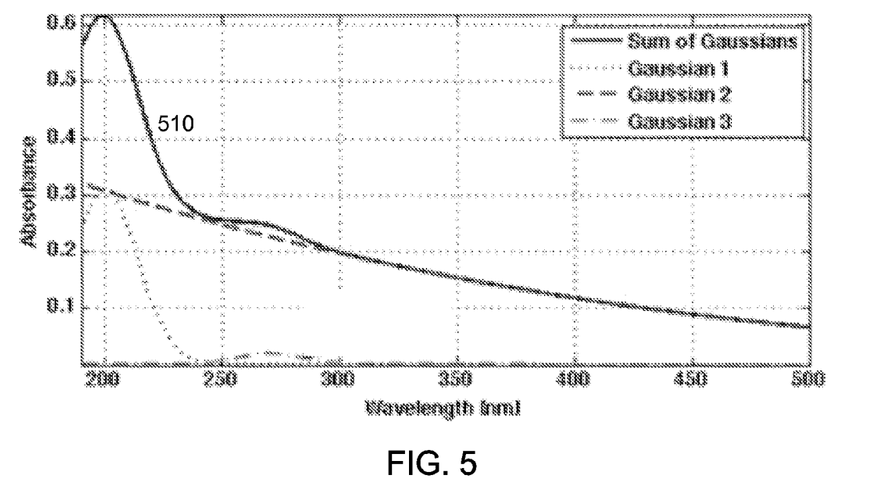
FIG. 5 is a graph illustrating curve fitting to an attenuation spectrum.

FIG. 5 illustrates curve fitting based on three Gaussians: one for the nitrate-nitrogen absorption peak at 200 nm (Gaussian 1), one for Rayleigh scattering (Gaussian 2) and one for organic carbon (Gaussian 3). The solid curve 510 shows the attenuation spectrum.

Other types of physical models can also be used. For example, it is possible to remove the soil interferences from UV measurements on soil nitrate-nitrogen by fitting a broad background on top of the narrow (~20 nm full width) absorption peak at 200 nm due to nitrate-nitrogen. Particular embodiments of the background fitting functions could include a polynomial background, one or more Gaussian backgrounds or an empirically derived function. The narrow peak due to nitrate-nitrogen can be characterized by first measuring pure nitrate-nitrogen in the extractant and then using these measured absorption peaks and widths as fitting constants when performing the measurement on soil-extractant mixtures.

In a different approach, the estimate of nitrate-nitrogen concentration can be determined empirically, for example based on a learning algorithm or other adaptive or self-organizing algorithm. A training set includes samples of attenuation spectra and their corresponding nitrate-nitrogen concentrations. The training set preferably covers the different variations expected in the field, for example different soil types and background contributions. This set is used to train the selected algorithm. A measured attenuation spectrum is then input to the trained algorithm, which estimates the nitrate-nitrogen concentration.

In one approach, partial least squares regression is used. In preliminary experiments, partial least squares regression was able to achieve +/−3.5 ppm accuracy. Note that an accuracy of 4 ppm for the nitrate-nitrogen concentration in soil corresponds to an accuracy of 0.2 ppm for the nitrate-nitrogen concentration in a 1:20 soil:water mixture. This would be acceptable for many types of analysis. Other types of principle components analysis can also be used.

Other sources of information can also be used. For example, if the soil type is known (e.g., sandy, silty, clay), that can be used as an input to estimate the nitrate-nitrogen concentration. Other factors such as pH, conductivity, soil:water mixture viscosity, soil moisture content, soil reflection spectrum, and soil density can also be used as inputs to estimate the nitrate-nitrogen concentration.

In some designs, in addition to estimating the nitrate-nitrogen concentration, the processor also indicates the confidence in the estimate. For example, if it is difficult to fit a certain attenuation spectrum, the processor might provide an estimate but also flag the sample as a bad fit. This might occur, for example, if the attenuation spectrum included an unknown interference. If necessary, these samples could then be discarded or sent to a lab for analysis.

Figure 6:
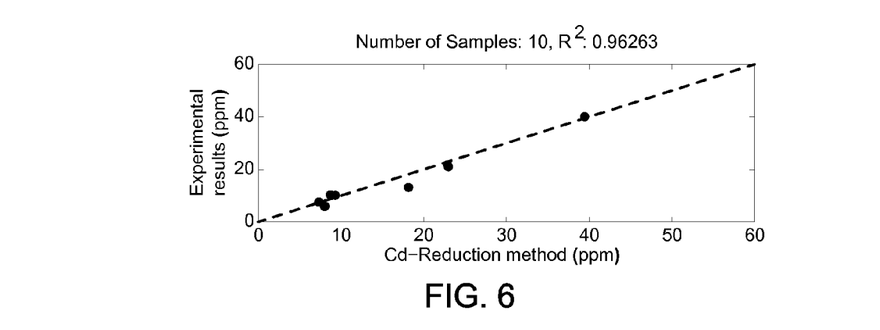
FIG. 6 is a graph summarizing experiments testing the accuracy of the invention.

FIG. 6 is a graph summarizing experiments. This experiment is based on ten soil samples, representing a variety of soil types (sand, loam, clay, etc). Each dot represents one sample. For each of these samples, the nitrate-nitrogen concentration was estimated using the approach described above (based on attenuation spectrum and the 200 nm absorption peak) and also using the standard Cd-reduction technique. The dashed line would be perfect correlation between the two techniques. The sample dots fall near the dashed line. These results indicate the viability of quickly and accurately predicting soil nitrate-nitrogen levels at commercially relevant levels using the technique described above.

Figure 7:
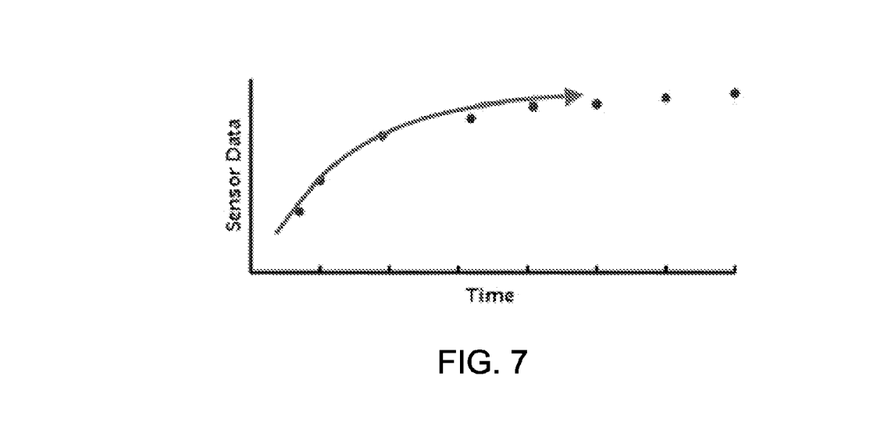
FIG. 7 is a graph of nutrient concentration as a function of time.

In some cases, when mixing soil with an extractant, it can take significant time for the nutrient or nutrients of interest to dissolve in the extractant. FIG. 7 is a graph of nutrient concentration (e.g., nitrate-nitrogen concentration) as a function of time, illustrating the time extrapolation of final concentrations of the nutrient. This can be used to improve the measurement speed.

UV-visible spectroscopy equipment can give accurate signals after measurement times much less than 1 second. The measurement of interest is often the final value after all of the relevant nutrients are part of the solution. The effective measurement time can be decreased by using data points, measured as a function of time, to predict the value at saturation before the measured values become steady.

Referring to FIG. 7, the process begins with the mixing of soil and extractant. The concentration of the nutrient of interest (e.g., nitrate-nitrogen concentration) is calculated at different times, thus yielding a plot of concentration vs time, as shown in FIG. 7. The data points are curve fit to a functional form that will predict the final answer (e.g., exponential or other asymptotic function). The curve fit is updated as more data points are collected. The error of the fit is also estimated. The soil measuring cycle is terminated when the estimated error is less than some threshold value, or after some set maximum measurement time has been exceeded. Referring to FIG. 7, in cases where the measurement system is much faster than the underlying extraction process, the fitting function can estimate the final value well before the extraction process actually reaches that value, thus reducing the time required to estimate concentration.

The process of fitting the data points can be done in a number ways. One approach involves least squares regression of the data point to a physically or chemically motivated formula for the time dependence. One such function is a constant minus an exponentially decreasing function. Another function is a polynomial as a function of time. Another function is some linear combination of these functional forms with various fitting parameters. An alternate approach for fitting the time dependence is the use of a machine learning algorithm trained on a large set of appropriately labeled data.

Parameters relating to the speed and shape of the time dependence fitting can also be provided. Examples of relevant parameters include measurements relating to the extractant/moisture content of the soil (correlating to the amount of nutrients that are already dissolved) and soil composition (percentage clay, silt, sand, organic matter, etc.) which relates to the physical extraction processes.

In various embodiments, the attenuation spectrum can be obtained by techniques other than propagating the light directly through the soil-extractant mixture. For example, evanescent-field fiber absorption spectroscopy or attenuated total reflection (ATR) are two alternate techniques to measure the attenuation spectrum.

In other aspects, the estimates of nitrate-nitrogen concentration are combined with other measurements. In one embodiment, an optical detector measures scattered light. This signal is used as an additional input to reduce the soil interferences, since small particulates (such as those found in a soil/extractant mixture) can strongly scatter light and thus interfere with optical transmission measurements.

Another embodiment could contain optical reflectivity measurements of the soil before extractant mixing in the UV, visible, near IR, and/or mid IR spectra. The reflectivity of dry soil as a function of wavelength is generally correlated to soil type. Such information can be used, in conjunction with the other embodiments discussed herein to provide data of interest to the end user, and for additional tests.

Another embodiment includes the integration of additional measurements such as soil moisture, soil conductivity, temperature, ambient humidity, soil pH, soil/extractant solution viscosity, etc. which are useful in their own right but can also be integrated with the above measurements to increase accuracy. For example, by measuring the moisture content of the soil, the nitrate-nitrogen measurement can be made more accurate by subtracting the weight of the water from the initial soil sample.

The approaches described above have many advantages. Certain implementations have the potential to combine the accuracy of lab-based soil sampling but at a significantly faster speed and lower cost. By measuring nitrate-nitrogen directly in the soil, the interferences that hinder indirect NDVI measurements are avoided. In addition, by using the 200 nm absorption peak rather than the 300 nm absorption peak, lower concentrations of nitrate-nitrogen can be measured. To be agronomically relevant, a nitrate-nitrogen measurement system generally should be able to accurately measure soil nitrate-nitrogen concentration in the range of 0-50 ppm. Furthermore, the approach described above can be implemented in a fast, portable instrument with no chemical reagents, thus offering a more timely and cost-effective high density analysis compared to soil chemistry labs. Field instruments can be used to essentially sample nitrate-nitrogen concentration in real-time with high density across a field.

This can allow growers to rapidly and economically measure soil nitrate-nitrogen levels, thus enabling them to improve their fertilizer management decisions. For example, split application of nitrogen (through side-dressing) can greatly improve nitrogen use efficiency. However, side-dressing is time sensitive, and management decisions of how much nitrogen to apply are often limited by the cost and slow turnaround of current soil testing procedures. Fertilizer is a significant agricultural cost and the inefficient use of fertilizer has large additional societal and environmental costs. Nitrous oxide arising from nitrogen-based fertilizer use is a significant cause of the driving force for global warming, and nitrogen runoff from agriculture causes serious water quality issues. Thus, improving fertilizer management will have large economic and environmental benefits.

Upon reading this disclosure, those of skill in the art will appreciate still additional alternative structural and functional designs. Thus, while particular embodiments and applications have been illustrated and described, it is to be understood that the present invention is not limited to the precise construction and components disclosed herein and that various modifications, changes and variations which will be apparent to those skilled in the art may be made in the arrangement, operation and details of the method and apparatus of the present invention disclosed herein without departing from the spirit and scope of the invention as defined in the appended claims.

What is claimed is:

1. A device for measuring a nitrate-nitrogen concentration in soil based on attenuation over a spectral operating range, the device comprising:
   a light source that generates light that spans the spectral operating range, the spectral operating range including wavelengths at least as short as 230 nm;
   a detector having a sensitivity that spans the spectral operating range;
   a sample chamber configured to contain a soil-extractant mixture, the light propagating from the light source to the detector and attenuated by the soil-extractant mixture in the sample chamber, the detector generating a soil spectral signal that indicates the light received by the detector at different wavelengths across the spectral operating range; and
   a processor coupled to the detector, wherein the processor estimates an attenuation spectrum of the soil-extractant mixture over the spectral operating range based on the soil spectral signal, and estimates the nitrate-nitrogen concentration based on the attenuation spectrum, wherein the processor, when estimating the attenuation spectrum, removes interference in the soil-extractant mixture using one of spectral deconvolution and curve-fitting.

2. The device of claim 1, wherein the spectral operating range includes wavelengths proximate a 200 nm nitrate-nitrogen absorption peak, and wherein the 200 nm nitrate-nitrogen absorption peak includes estimated attenuation values for wavelengths greater than 200 nm.

3. The device of claim 1, wherein the sample chamber is optically positioned between the light source and the detector, the light propagating through the soil-extractant mixture in the sample chamber.

4. The device of claim 1, wherein the processor estimates the attenuation spectrum based on the soil spectral signal, a reference spectral signal and a dark spectral signal, wherein the reference spectral signal is generated when the sample chamber contains extractant without soil and the dark spectral signal is generated without light from the light source incident on the detector.

5. The device of claim 1, wherein, at different times, the sample chamber contains the soil-extractant mixture or extractant without soil, the detector generating the soil spectral signal when the sample chamber contains the soil-extractant mixture and the detector generating a reference spectral signal when the sample chamber contains extractant without soil, the processor estimating the attenuation spectrum based on the soil spectral signal and the reference spectral signal.

6. The device of claim 1, further comprising:
   a second sample chamber configured to contain extractant without soil, wherein the processor estimates the attenuation spectrum based on the soil spectral signal and a reference spectral signal, wherein the reference spectral signal is generated from the second sample chamber containing extractant without soil.

7. The device of claim 1, further comprising:
a reference optical path from the light source to the detector but not attenuated by the soil-extractant mixture, wherein the processor estimates the attenuation spectrum based on the soil spectral signal and a reference spectral signal, wherein the reference spectral signal is generated based on the reference optical path.

8. The device of claim 1 wherein the processor curve fits the attenuation spectrum, at least one component of the curve fit based on a nitrate-nitrogen 200 nm absorption peak.

9. The device of claim 1 wherein the processor receives a soil type and estimates the nitrate-nitrogen concentration further based on the soil type.

10. The device of claim 1 wherein the processor receives a soil conductivity and estimates the nitrate-nitrogen concentration further based on the soil conductivity.

11. The device of claim 1, wherein the processor applies a partial least squares regression to the attenuation spectrum to estimate the nitrate-nitrogen concentration.

12. The device of claim 1, wherein the processor is trained based on a set of absorption spectra and their corresponding nitrate-nitrogen concentrations, and the processor estimates the nitrate-nitrogen concentration based on its training.

13. The device of claim 1, wherein the processor curve fits the attenuation spectrum, at least one component of the curve fit based on a Gaussian background spectrum.

14. The device of claim 1, wherein the processor estimates the nitrate-nitrogen concentration as a function of time of measurement and extrapolates the estimates to a final estimated nitrate-nitrogen concentration.

15. The device of claim 1, wherein a UV spectrum of the light source can be controlled separately from a visible spectrum of the light source.

16. The device of claim 15, wherein the light source includes two bulbs, one of which has a relatively stronger UV spectrum than the other, and which can be separately controlled.

17. The device of claim 1, further comprising:
a filter that filters the soil-extractant mixture, the light propagating through the filtered soil-extractant mixture.

18. The device of claim 1, wherein the light propagates through unfiltered soil-extractant mixture.

19. The device of claim 1, further comprising:
a centrifuge for separating the soil-extractant mixture, the light propagating through the separated soil-extractant mixture.

20. A method for measuring the nitrate-nitrogen concentration in soil based on attenuation over a spectral operating range, the method comprising:
generating light that spans the spectral operating range and includes wavelengths at least as short as 230 nm;
providing a soil-extractant mixture that attenuates the light;
detecting the attenuated light;
generating a soil spectral signal that indicates the light detected at different wavelengths across the spectral operating range;
estimating an attenuation spectrum of the soil-extractant mixture over the spectral operating range based on the soil spectral signal, wherein estimating the attenuation spectrum includes removing interference in the soil-extractant mixture using one of spectral deconvolution and curve-fitting; and
estimating the nitrate-nitrogen concentration based on the attenuation spectrum.

21. A device for measuring the nitrate-nitrogen concentration in soil based on attenuation over a spectral operating range, the device comprising:
a light source that generates light that spans the spectral operating range, wherein the spectral operating range includes wavelengths at least as short as 230 nm;
a detector having a sensitivity that spans the spectral operating range;
a sample chamber configured to contain a soil-extractant mixture, wherein the light propagates from the light source to the detector and is attenuated by the soil-extractant mixture in the sample chamber, wherein the detector generates a soil spectral signal that represents the light received by the detector at different wavelengths across the spectral operating range; and
a processor coupled to the detector, wherein the processor estimates an attenuation spectrum of the soil-extractant mixture over the spectral operating range based on the soil spectral signal, a reference spectral signal and a dark spectral signal, wherein the processor estimates the nitrate-nitrogen concentration based on the attenuation spectrum.

22. A method for measuring the nitrate-nitrogen concentration in soil based on attenuation over a spectral operating range, the method comprising:
generating light that spans the spectral operating range, the spectral operating range including wavelengths at least as short as 230 nm;
providing in a sample chamber, a soil-extractant mixture that attenuates the light;
detecting the attenuated light with a detector;
generating a soil spectral signal that indicates the light detected at different wavelengths across the spectral operating range;
estimating an attenuation spectrum of the soil-extractant mixture over the spectral operating range based on the soil spectral signal, a reference spectral signal and a dark spectral signal, wherein the nitrate-nitrogen concentration is estimated based on the attenuation spectrum.

* * * * *